(12) United States Patent
Lauf (10) Patent No.: US 9,068,440 B1
(45) Date of Patent: Jun. 30, 2015

(54) EXPLOSION-PROOF MAGNETIC FLUX LEAKAGE INSPECTION APPARATUS FOR WELL TUBING

(76) Inventor: William Lauf, Vernal, UT (US)

(*) Notice: Subject to any disclaimer, the term of this patent is extended or adjusted under 35 U.S.C. 154(b) by 273 days.

(21) Appl. No.: 13/524,334

(22) Filed: Jun. 15, 2012

Related U.S. Application Data (60) Provisional application No. 61/654,640, filed on Jun. 1, 2012.

(51) Int. Cl.
| | |
|---|---|
| G01N 27/82 | (2006.01) |
| E21B 47/10 | (2012.01) |
| G01R 33/12 | (2006.01) |
| G01N 27/72 | (2006.01) |

(52) U.S. Cl.
CPC .............. *E21B 47/102* (2013.01); *G01R 33/12* (2013.01); *G01N 27/82* (2013.01); *G01N 27/72* (2013.01)

(58) Field of Classification Search
CPC .......... G01N 27/82; G01N 2291/2634; G01N 27/83; E21B 47/102; G01R 33/12
USPC .................................................. 324/221–243
See application file for complete search history.

(56) References Cited

U.S. PATENT DOCUMENTS

| | | | | |
|---|---|---|---|---|
| 2,895,103 | A * | 7/1959 | Vogt et al. ...................... | 324/260 |
| 3,328,681 | A * | 6/1967 | Wood ............................. | 324/225 |
| 4,629,991 | A * | 12/1986 | Wheeler ........................ | 324/232 |
| 6,924,640 | B2 | 8/2005 | Fickert et al. | |
| 2009/0323247 | A1 * | 12/2009 | Schmidt ........................ | 361/160 |

* cited by examiner

*Primary Examiner* — Melissa Koval
*Assistant Examiner* — Daniel Miller
(74) *Attorney, Agent, or Firm* — James R. Young; Cochran Freund & Young LLC (57) ABSTRACT

Explosion-proof magnetic flux leakage inspection apparatus for well tubing includes a hermetically sealed interior chamber with an inner wall assembly that forms and surrounds a central channel in a manner that separates the central channel from the hermetically sealed interior chamber by the inner wall assembly. The central channel has an open top and an open bottom to accommodate passage of the well tubing through the central channel. An electromagnetic coil, magnetic flux leakage detector assembly, and a shallow reading detector assembly are positioned in the hermetically sealed interior chamber around the inner wall assembly.

5 Claims, 7 Drawing Sheets

EXPLOSION-PROOF MAGNETIC FLUX LEAKAGE INSPECTION APPARATUS FOR WELL TUBING

BACKGROUND OF THE INVENTION

1. Technical Field of the Invention

This invention is related to magnetic flux leakage testing for flaws in well tubing.

2. State of the Prior Art

Oil and gas wells, water wells, injection wells, and other kinds of wells drilled into the ground are often lined with pipe casing that is cemented into the well hole to protect the well hole from pressures and debris and to isolate various geological strata and fluid zones from other over-laying and under-laying strata and fluid zones. Many of such wells are completed for production with tubing strings, e.g., lengths of smaller diameter pipes (tubing) fastened together and lowered into the well through the casing. Various items of completion equipment can be included in the tubing strings, such as packers, bridge plugs, valves, pumping apparatus, and other devices, depending the particular characteristics and functions of the well. Other well completion steps, such as perforating the casing into reservoir production zones, hydraulic fracturing, work-over cementing and re-perforating into new reservoir zones, and the like can be performed through the tubing. In oil and gas wells, the oil and gas produced from various production zones in the well may be flowed through the tubing to the surface of the well. In injection wells, water or other fluids may be injected into subsurface reservoirs through the tubing. Over time, flaws can develop in such tubing due to rust or other corrosion, fatigue, mechanical impacts, scratches, gouges, wear, and other instrumentalities that can be manifested, for example, in pits, buns, holes, cracks, reduced wall thicknesses, and other forms of metal loss or abnormalities on inside surfaces of the tubing, outside surfaces, or both. Such flaws, if severe enough, can degrade the integrity of the tubing and potentially result in failure, for example, leaks, bursting, collapse, or breakage, which can adversely affect the operation of the well or cause expensive shutdowns for repairs.

Magnetic flux leakage testing is a common technique used for non-invasive inspection of steel and other kinds of ferromagnetic metal pipes to find flaws or defects before they become severe enough to cause failure. The terms "flaw" and "defect" are synonymous for this description and may be used interchangeably According to the technique, a powerful magnet is used to magnetize portions of the ferromagnetic pipe or tubing, preferably, but not necessarily, to magnetic saturation. Damaged or flawed areas of the tubing in which there has been metal loss, such as the flaws discussed above, cannot support as much magnetic flux as undamaged areas. Therefore, at locations in the ferromagnetic tubing wall where there are flaws, the magnetic field "leaks" from the ferromagnetic material and can be detected and measured. Hall effect transducers, coils, or other sensors positioned adjacent the magnetically saturated tubing can be used to produce a voltage that is indicative of the strength of the magnetic field, thus can detect and measure perturbations in the magnetic field adjacent the tubing caused by such magnetic flux leakage.

Shallow reading sensors (sometimes called wall sensors) used in conjunction with the magnetic flux leakage detectors can be used to determine whether the detected flaw is on the tubing surface that is adjacent to the magnetic flux leakage detectors or on the opposite surface. Shallow reading sensors detect flaws in the surface adjacent to the magnetic flux leakage detectors. Therefore, if a flaw is sensed by both the magnetic flux leakage detector and the shallow reading detector, the flaw is deduced to be located in the surface of the ferromagnetic tubing adjacent to the magnetic flux leakage detectors. However, if a flaw is sensed by the magnetic flux leakage detector but not by the shallow reading detector, then the flaw can be deduced to be located in the opposite surface of the ferromagnetic tubing. Typical shallow reading sensors include reluctance sensors and eddy current sensors. An example reluctance detector may comprise a coil and a small magnet combination that responds to changes in the magnetic field resulting from a perturbing defect or flaw on the tubing surface adjacent the magnetic flux leakage detectors. Hall effect sensors can also be used to as reluctance sensors. An example eddy current sensor for sensing eddy currents caused by flaws on the surface of the ferromagnetic material that is adjacent to the magnetic flux detectors may include a coil that detects magnetic field effects induced by the eddy currents resulting from the flaws on the surface of the ferromagnetic tubing.

Configurations of magnetic flux leakage detector apparatus are available commercially for use inside pipes and tubings, for example, the U.S. Pat. No. 6,924,640, which are sometimes called internal magnetic flux leakage detectors. Other configurations of magnetic flux leakage detector apparatus are available for use on the outsides of pipes and other ferromagnetic objects, sometimes called external magnetic flux leakage detectors. Internal magnetic flux leakage detector apparatus generally comprise a magnetic field generator, magnetic leakage detectors, shallow reading detectors, and data collection circuits packaged together in a module that is sized and shaped for traveling through the interior of pipe to be inspected, such as pipelines, well casings, well tubing strings, and the like. The magnetic field generator creates a strong magnetic field to magnetize the pipe from the inside, and the sensors detect the perturbations in the magnetic field as the apparatus moves through the pipe to detect flaws in the pipe as explained above. External magnetic flux leakage detector apparatus generally comprise similar magnetic field generator, sensor, and data collection components, but are shaped for travel along outer surfaces of pipes, so the magnetization of the pipe and detector sensing is provided adjacent to the outside surfaces of the pipe.

Well production tubing must be pulled out of wells occasionally (sometimes called "tripping pipe" or "tripping tubing") for various maintenance, repairs, re-completions to different reservoir zones, and other purposes. Therefore, external magnetic flux leakage detection equipment has been developed and used for performing magnetic flux leakage inspection for flaws on such well tubing as the well tubing is being pulled out of the well, so that individual pipe or tubing sections that have flaws of a sufficient severity to be problematic can be identified and marked or set aside. Some of such magnetic flux leakage inspection equipment is designed and configured for setting on a workover or pulling rig floor above the well head in a position for the rig to pull the pipe or tubing sections through the magnetic flux leakage detector apparatus as the pipe or tubing is pulled out of the well.

The foregoing examples of related art and limitations related therewith are intended to be illustrative, but not exclusive or exhaustive, of the subject matter. Other aspects and limitations of the related art will become apparent to those skilled in the art upon a reading of the specification and a study of the drawings.

BRIEF DESCRIPTION OF THE DRAWINGS

The accompanying drawings, which are incorporated herein and form a part of the specification, illustrate some, but not the only or exclusive, example embodiments and/or features. It is intended that the embodiments and figures disclosed herein are to be considered illustrative rather than limiting.

In the drawings.

DETAILED DESCRIPTION OF EXAMPLE EMBODIMENTS

An example magnetic flux leakage (MFL) inspection apparatus 10 for well tubing is shown in an example setting on a well workover or pulling rig floor F as tubing T is being tripped out of a well W, but recognizing that the invention recited in the claims below can also be implemented in myriad other ways, once the principles are understood from the description herein. This example implementation is made to be explosion-proof to prevent electrical sparks, gas from the well, impacts, and other instrumentalities from causing an explosion to occur in the MFL inspection apparatus 10 as it is being operated on the rig floor F.

Figure 1:
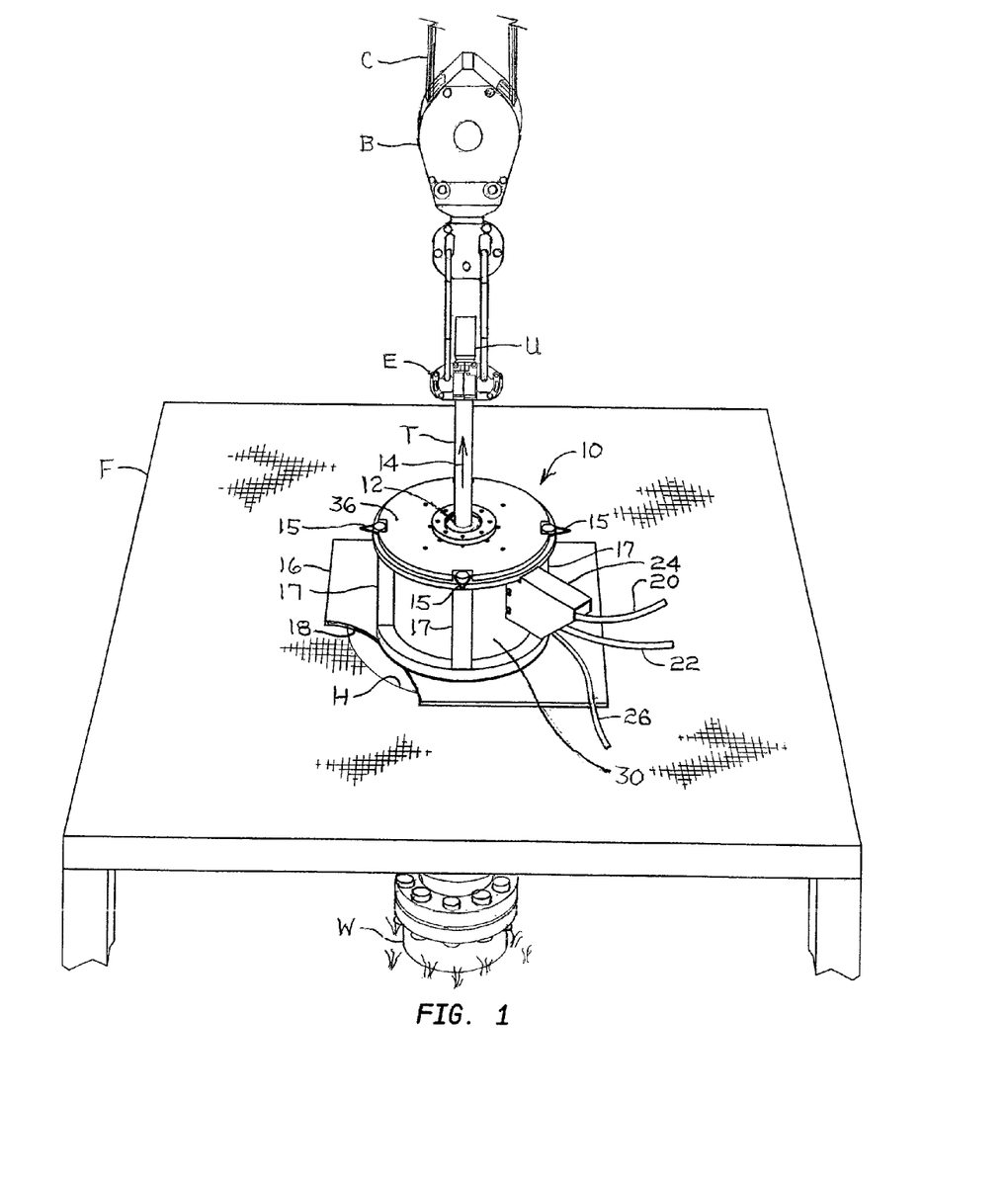
FIG. 1 is a perspective view of an example magnetic flux leakage inspection apparatus for well tubing shown in an example setting on a well workover rig floor as tubing is being tripped out of a well.
Figure 2:
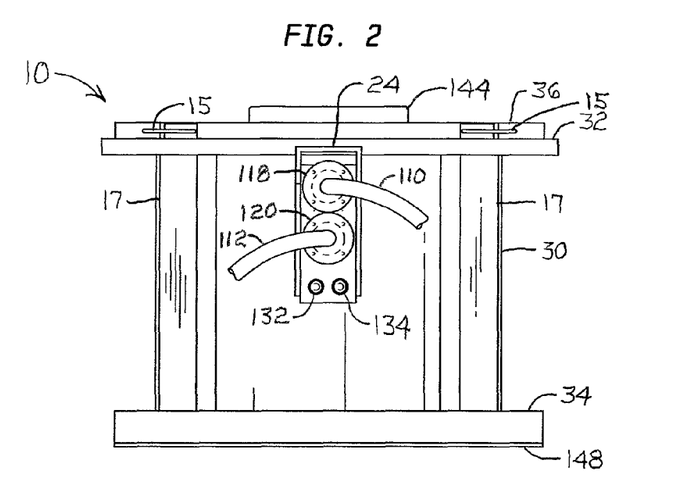
FIG. 2 is a front elevation view of the example magnetic flux leakage inspection apparatus in FIG. 1.

As illustrated in FIG. 1, the MFL inspection apparatus 10 is positioned on the rig floor F over the well W with the well tubing T extending through a central channel 12 in the MFL inspection apparatus, as will be described in more detail below. The example MFL inspection apparatus 10 is shown in FIG. 1 set on a float plate 16 over the floor hole H in the rig floor F. A notch 18 in the float plate 16 can be provided to allow the rig operator to observe slips (not shown) on the well W under the floor F when the float plate 16 and MFL inspection apparatus 10 are in place. Lift links 15 are connected to reinforcing ribs 17 and provided for attaching lift chains (not shown) for winching the MFL inspection apparatus 10 onto and off the rig floor F during set-up and take-down. Electrical cords 20, 22 provide electric power to the MFL inspection apparatus 10 and conduct data from the MFL inspection apparatus to an operator panel, display, or other output or storage device (not shown). The electrical connections of the electrical cords 20, 22 to the MFL inspection apparatus 10 are made with explosion-proof connectors (not seen in FIG. 1), which are protected by a shield 24 from accidental impacts by other equipment, tubing joints, and the like. Although the interior of the MFL inspection apparatus is sealed from the outside environment, as will be described in more detail below, a constant supply of pressurized air or inert gas can be provided to the interior by a supply hose 26 from a pressurized air or inert gas source or pump to prevent ingress and build-up of flammable gas or other explosive substances from the well W into the interior during operation.

In operation, the rig elevator E is attached to the tubing T joints above the MFL inspection apparatus 10, as illustrated in FIG. 1, and the tubing T is then pulled upwardly through the MFL inspection apparatus 10 by the rig draw cable C, traveling block B, and elevator E, as indicated by the arrow 14, as the tubing T is tripped out of the well W in a normal manner. As the tubing T joints are pulled upwardly through the MFL inspection apparatus, the MFL inspection apparatus magnetizes the tubing T, which is ferromagnetic, and the magnetic flux leakage detectors (not seen in FIG. 1) detect flaws in the tubing T. Concurrently, shallow reading sensors (sometimes called wall sensors) (not seen in FIG. 1) detect only flaws on the exterior surface of the tubing T, which indicates whether the flaws detected by the magnetic flux leakage detectors are on the exterior surface or on the interior surface of the tubing T. The sensor measurements are logged, processed, and reported or displayed to an operator on a display panel (not shown), and any tubing T joints that are indicated to have flaws that exceed predetermined parameters can be marked or set aside for refurbishing or disposal.

Figure 6:
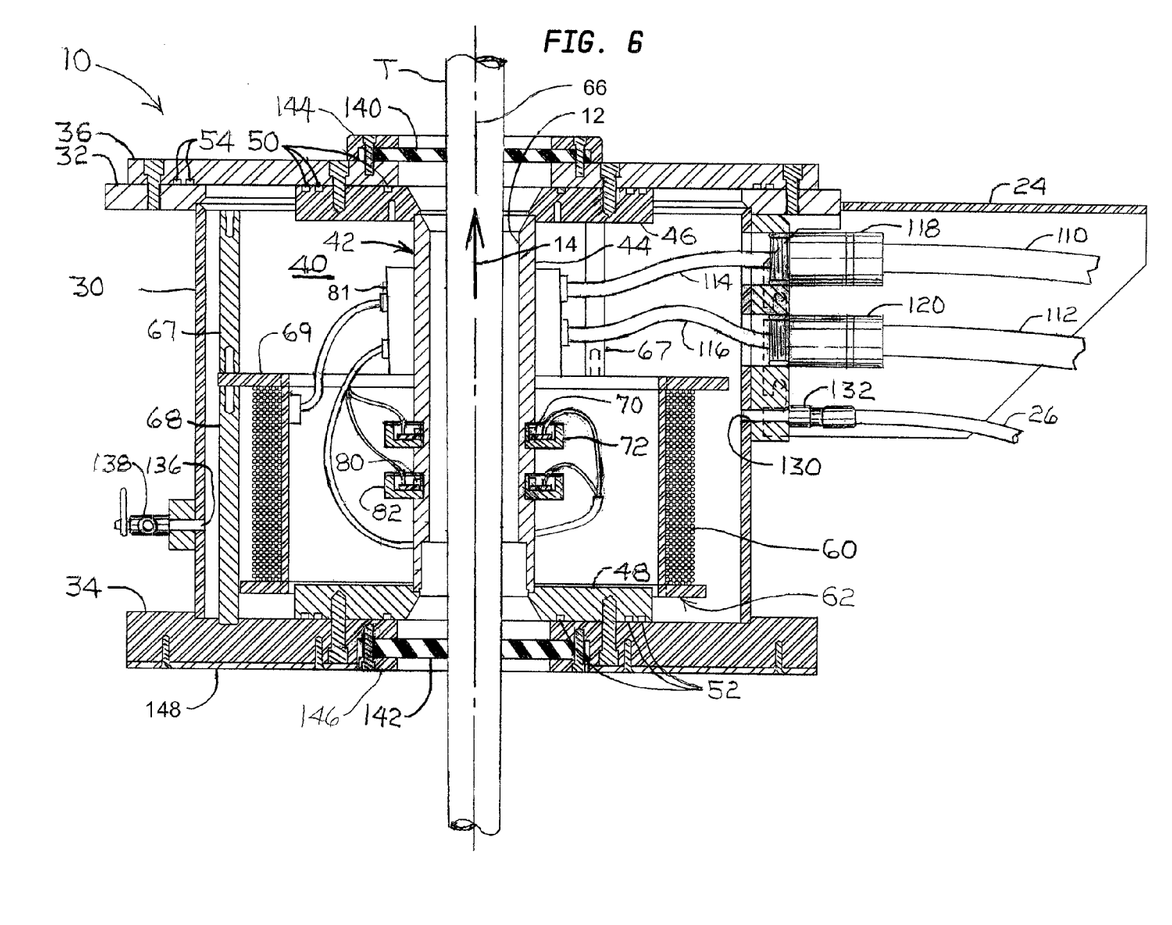
FIG. 6 is a cross-section view of the example magnetic flux leakage inspection apparatus taken along section line 6-6 in FIG. 5.
Figure 7:
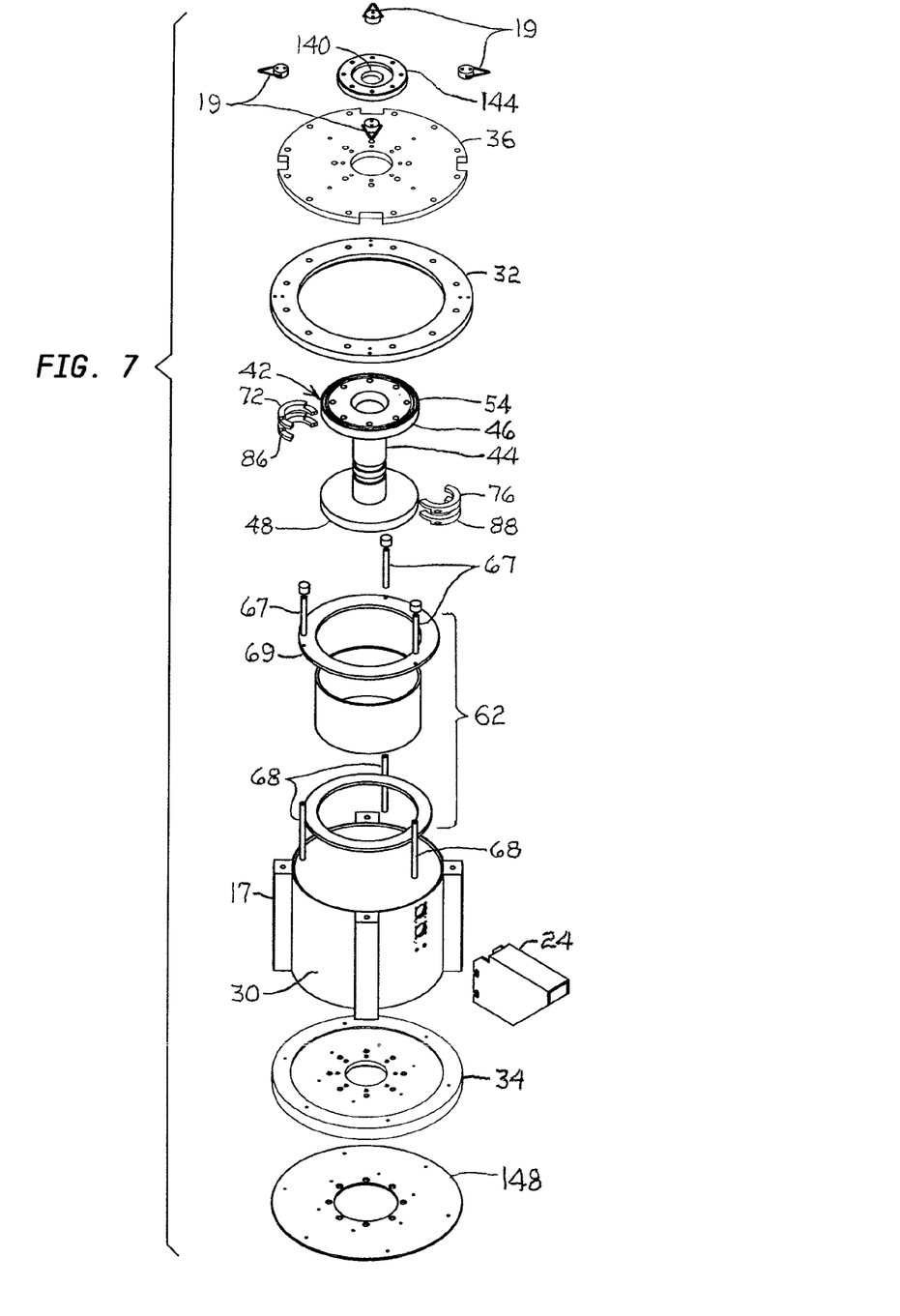
FIG. 7 is an exploded view of the component parts of the example magnetic flux leakage inspection apparatus in FIG. 1.

Referring now primarily to FIG. 6 in combination with FIGS. 1-5 and 7, the example MFL inspection apparatus 10 comprises an outer wall (e.g., a cylindrical barrel wall 30) between a top closure (e.g., a top cover 36) and a bottom closure (e.g., a bottom barrel flange 34) to surround an interior chamber 40. In the example apparatus 10, the top cover 36 is mounted on a top barrel flange 32 on the top rim of the barrel wall 30. The interior chamber 40 is further enclosed by an inner wall assembly 42, which surrounds the central channel 12 and is connected to the top cover 36. The inner wall assembly 42 is mounted on the bottom flange 34, and the top cover plate 36 is mounted on the top barrel flange 32 and on the inner wall assembly 42. The inner wall assembly 42 comprises an elongated conduit 44, which forms the central channel 12 and is terminated at the top end with a top conduit flange 46 and at the bottom end with a bottom conduit flange 48. One or more top center seals 50 (e.g., O-ring seals) are positioned between the top conduit flange 46 and the cover plate 36 to prevent flammable gases, liquids, or other substances that get into the central channel 12, (e.g., from the well W) from migrating into the interior chamber 40. Similarly, one or more bottom center seals 52 (e.g., O-ring seals) are positioned between the bottom conduit flange 48 and the bottom barrel flange 34 to prevent flammable gases, liquids, or other substances that get into the central channel 12, (e.g., from the well W) from migrating into the interior chamber 40 One or more top outer seals 52 (e.g., O-ring seals) are positioned between the top flange 32 and the cover plate 36 to prevent flammable gases, liquids, or other substances that may be around the outside of the MFL inspection apparatus 10 from migrating into the inner chamber 40. The joint between the conduit 44 and the top conduit flange 46 as well as the joint between the conduit 44 and the bottom conduit flange 48 can be welded to seal against ingress of any flammable gases, liquids, or other substances from outside into the interior chamber 40 through those joints. Likewise, the joint between the barrel wall 30 and the top barrel flange 32 as well as the joint between the barrel wall 30 and the bottom barrel flange 34 can be welded to seal against ingress of any flammable gases, liquids, or other substances from outside the MFL inspection apparatus 10 into the interior chamber 40. Consequently, the interior chamber 40 is effectively hermetically sealed from the center channel 12 and from the outside environment.

An electromagnetic coil 60 is wound on a spool 62 and positioned in the hermetically sealed interior chamber 40. The coil 60 creates a magnetic field that magnetizes the portion of the tubing T in the central channel 12. The spool 62 with the coil 60 can be mounted in the interior chamber 40 concentric with the longitudinal axis 66 of the central channel 12 and conduit 44 in any convenient manner, for example, with a plurality of upper coil mounting legs 67 and lower coil mounting legs 68, both of which fasten to the upper flange 69 of the spool 62 as best seen in FIG. 6. The inner wall assembly 42, including, but not limited to, the conduit 44, is made of a non-magnetic material, for example, aluminum, so that it does not interfere with or divert the magnetic field created by the coil 60. Other components of the MFL inspection apparatus 10 are also made of non-magnetic material, for example, aluminum, including, for example, the barrel wall 30, flanges 32, 34, and cover plate 36, so that those components also do not interfere with, or divert, the magnetic field. Consequently, the magnetic flux in the magnetic field is concentrated in the section of the tubing T that is in the central channel 12. It is preferable, although not essential, that the magnetic field is strong enough to saturate the section of the tubing T that is in the central channel 12 to ensure that flaws in the tubing T cause sufficient magnetic flux leakage to be detectable by a magnetic flux leakage detector assembly, for example, the split ring detector assembly 72 comprising magnetic field flux leakage sensors 70, mounted in the interior chamber 40 in a manner that surrounds the tubing T in the central channel 12, as best seen in FIG. 6 in combination with FIGS. 8A and 8B. A shallow reading assembly, for example, the split-ring shallow reading assembly 82 comprising shallow reading sensors 80 (FIG. 6) is also mounted in the interior chamber 40 on the conduit 44 in a manner that surrounds the tubing T in the central channel, as best seen in FIG. 6 in combination with FIGS. 8A and 8B. As mentioned above, the shallow reading sensors 80 detect flaws in the surface of the tubing T that is nearest the shallow reading sensors 80, which, as shown in FIG. 6, is the outside surface of the tubing T. Therefore, if a flaw is sensed by both a magnetic flux leakage detector 70 and a shallow reading sensor 80, the flaw can be deduced to be on the outside surface of the tubing T. On the other hand, if a flaw is sensed by only the magnetic flux leakage detector 70 and not by a shallow reading sensor 80, then the flaw can be deduced to be on the inside surface of the tubing T.

Figure 8A:
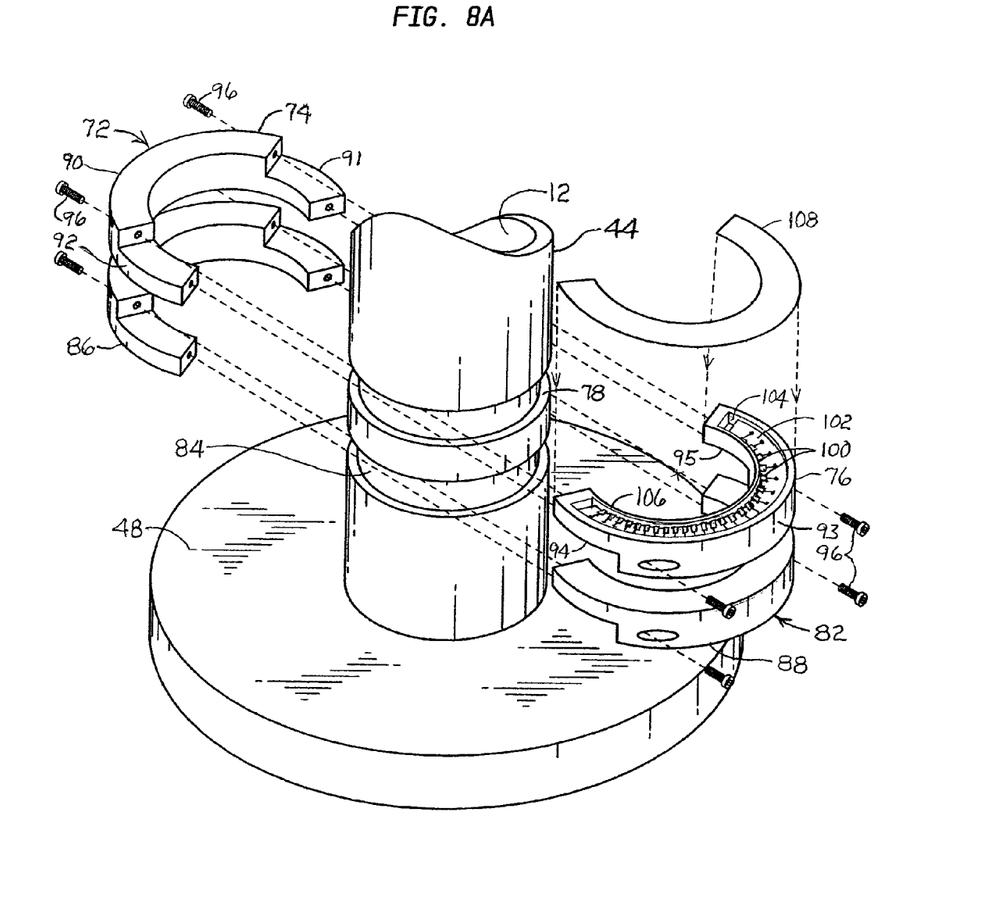
FIG. 8A is an enlarged, isometric view of the central channel housing and sensor assembly of the example magnetic flux leakage inspection apparatus in FIG. 1.
Figure 8B:
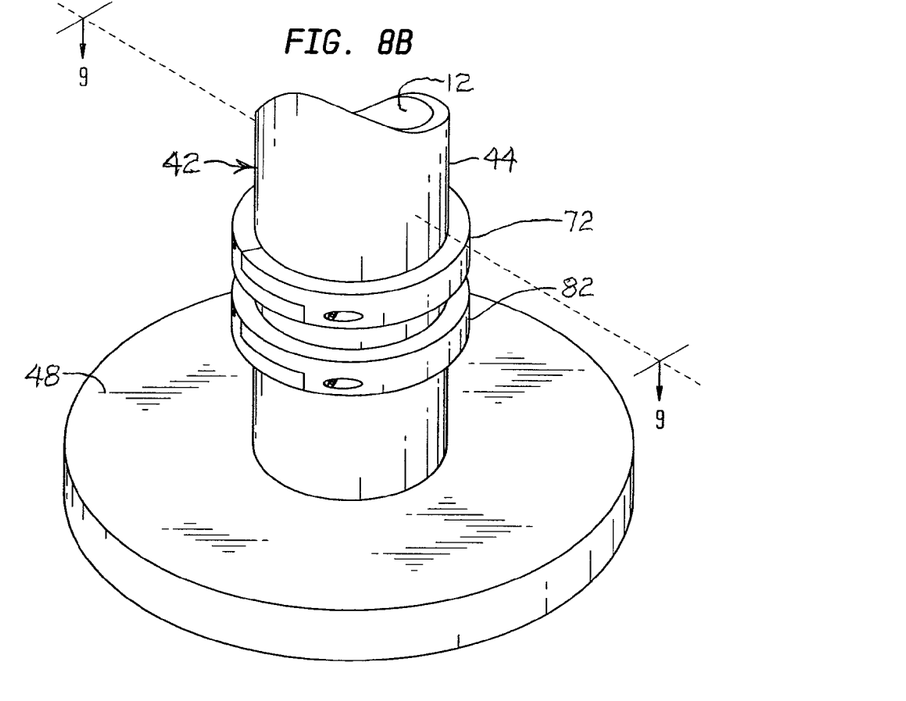
FIG. 8B is an enlarged, isometric view of the central channel housing and sensor assembly of the example magnetic flux leakage inspection apparatus similar to FIG. 8A but with the sensors of the assembly mounted on the central channel housing.

Referring now primarily to FIG. 8A, an example split ring magnetic flux leakage detector assembly 72 comprises two half-ring sections 74, 76 that are sized and shaped to mate together in a fitting relationship as they fit and are mounted in a circumferential groove 78 in the conduit 44. One half-ring section 74 is arc-shaped with a thicker mid-portion 90 and thinner, extending, opposite end portions 91, 92. Likewise, the other half-ring section 76 is similarly arc-shaped with a thicker mid-portion 93 and thinner, extending, opposite end portions 94, 95. The thinner end portions 91, 92 of the half-ring section 72 slip under the thinner end portions 94, 95, respectively, of the half-ring section 74 and into abutting relation with the thicker mid-portion 93 of the half-ring section 76. At the same time, the thinner end portions 94, 95 of half-ring section 93 slip over the thinner end portions 91, 92 of the half-ring section 74 and into abutting relation with the thicker mid-portion 90 of the half-ring section 74. The half-ring sections 72, 76 are fastened together in that relationship in the groove 78, for example, by fasteners 96, which may be screws as shown in FIG. 8A or any other convenient fastening mechanism, adhesive, or other instrumentality.

As shown in FIG. 8A, the example split ring magnetic flux leakage detector assembly 72 has a plurality of Hall effect sensors 100 on an arc-shaped printed circuit board 102 mounted in an arc-shaped cavity 104 in the half-ring section 76. The cavity 104 is formed in the half-ring section 76 in a manner that leaves only a thin inner wall 106 so that the Hall effect sensors 100 mounted on the inner edge of the arcuate printed circuit board 102 adjacent to the thin inner wall 106 are close to the tubing T in the central channel 12 (FIG. 6) when the split-ring magnetic flux leakage detector assembly 72 is mounted in the groove 78. The groove 78 also has the effect of thinning the conduit 44 in the groove 78, which also allows the Hall effect sensors 100 to be positioned radially closer to the tubing T in the central channel 12, which enhances the ability of the Hall effect sensors 100 to sense perturbations in the magnetic field caused by magnetic flux leakage that results from flaws in the tubing T. The number of Hall effect sensors can be a matter of design choice, depending on the diameter of the tubing T and the flaw detection resolution desired. For 2 to 4 inch tubing, sufficient resolution may be obtained with, for example, 40 to 80 Hall effect sensors. A cover 108 can be provided to close the cavity 104 over the printed circuit board 102 to protect the Hall effect sensors and electronics on the printed circuit board 102. For example, the cover 108 can be a thin plastic sheet adhered to the top surface edges of the half-ring section 76. The other half-ring section 74 has a similar structure, arcuate cavity, arcuate printed circuit board, Hall effect sensors, and electronic circuit components as the half-ring section 74, but they are not visible in FIG. 8A.

Figure 9:
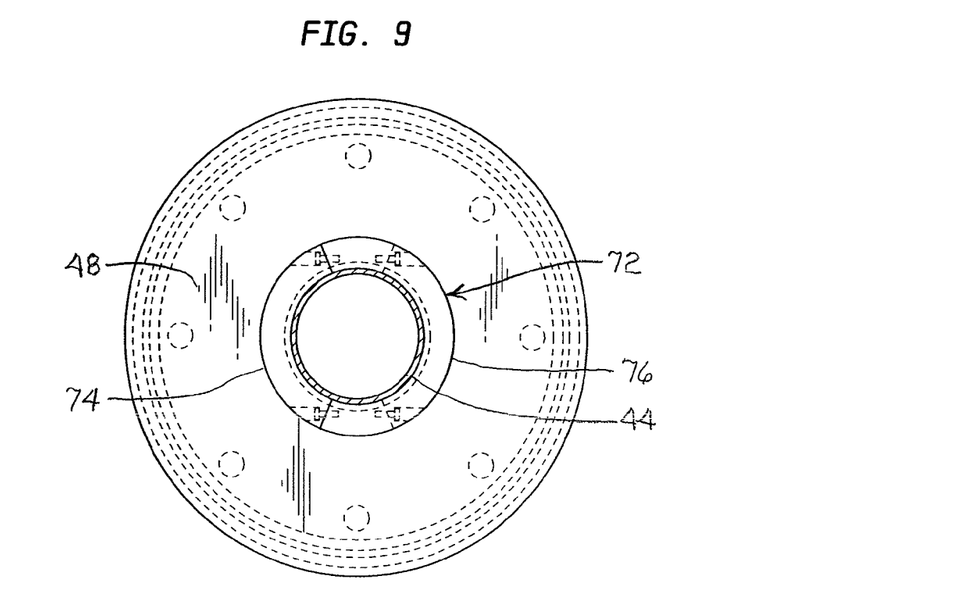
FIG. 9 is cross-section view of the central channel housing in FIGS. 8A and 8B taken along section line 9-9 in FIG. 8B.

The shallow reading sensors 80 (FIG. 6) are also mounted in a split-ring shallow reading detector assembly 82, which is similar to the split-ring magnetic flux leakage sensor assembly 72 as illustrated, for example, in FIG. 8A. The split-ring shallow reading detector assembly 82, comprising two half-ring sections 86, 88, also mounts in a circumferential groove 84 in the surface of the conduit 44. The Shallow reading sensors 80 (FIG. 6, not seen in FIG. 8A) can be Hall effect sensors, coils, or other sensor components as explained above, and they can be mounted on a printed circuit board in an arcuate cavity in a similar manner to that described above for the Hall effect sensors 100. The magnetic flux leakage detector assembly 72 and the shallow-reading detector assembly 82 are shown mounted on the conduit 44 in FIGS. 6, 8B, and 9. Fewer Hall effect sensors, for example 4 to 16, may be sufficient for the shallow reading detector assembly, but any number that provides the resolution desired can be provided in the shallow reading detector assembly 82.

Maintaining a constant distance between the tubing T and the Hall effect sensors 70 is important to obtaining accurate and reliable sensing and quantifications of flaws in the tubing T. As best seen in FIG. 6, a top bushing 140 and a bottom bushing 142 made of resiliently stiff rubber or other suitable material are provided at the bottom opening and at the top opening, respectively, to guide and maintain the tubing T in the middle of the conduit 44 concentric with the longitudinal axis 66 of the central channel 12. The bushings 140, 142 are stiff enough to maintain the tubing T in the middle of the conduit 44 as the tubing T is being pulled through the central channel 12, but they are also resiliently yieldable enough to allow passage of larger diameter tubing upsets U (FIG. 1), collars, couplings, and other larger diameter tubing components (not shown) through the central channel 12. The top bushing 140 in the example MFL inspection apparatus 10 is held in place by a top bushing retainer 144, and the bottom bushing 142 is held in place by a bottom bushing retainer 146. A wear plate 148 is mounted on the bottom of the bottom barrel flange 34 to protect the flange 34 and bottom bushing retainer 146.

Figure 3:
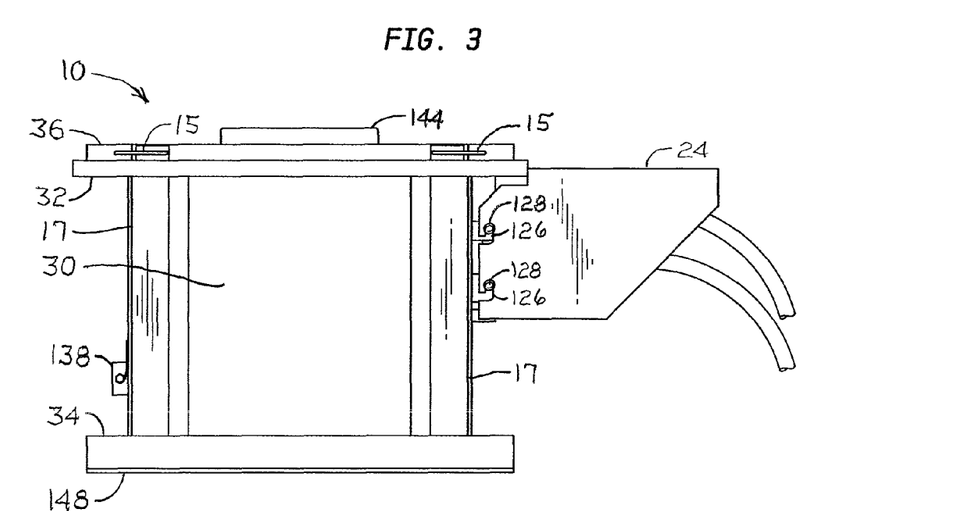
FIG. 3 is a side elevation view of the example magnetic flux leakage inspection apparatus in FIG. 1.
Figure 4:
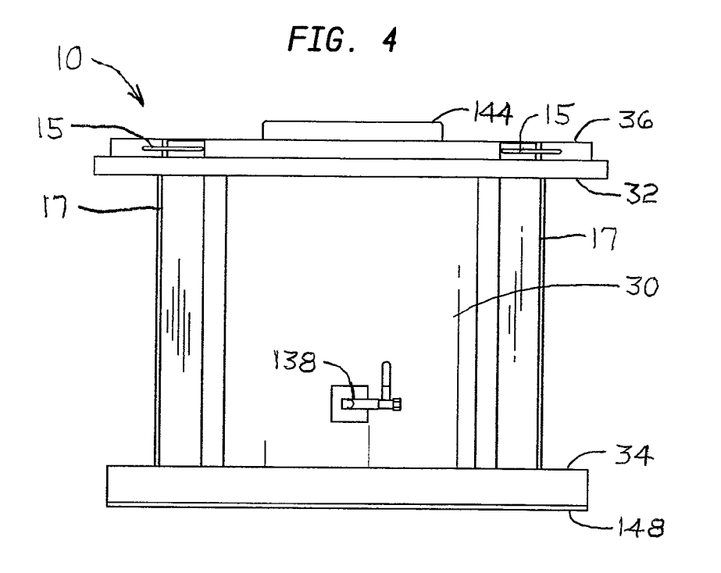
FIG. 4 is a rear elevation view of the example magnetic flux leakage inspection apparatus in FIG. 1.
Figure 5:
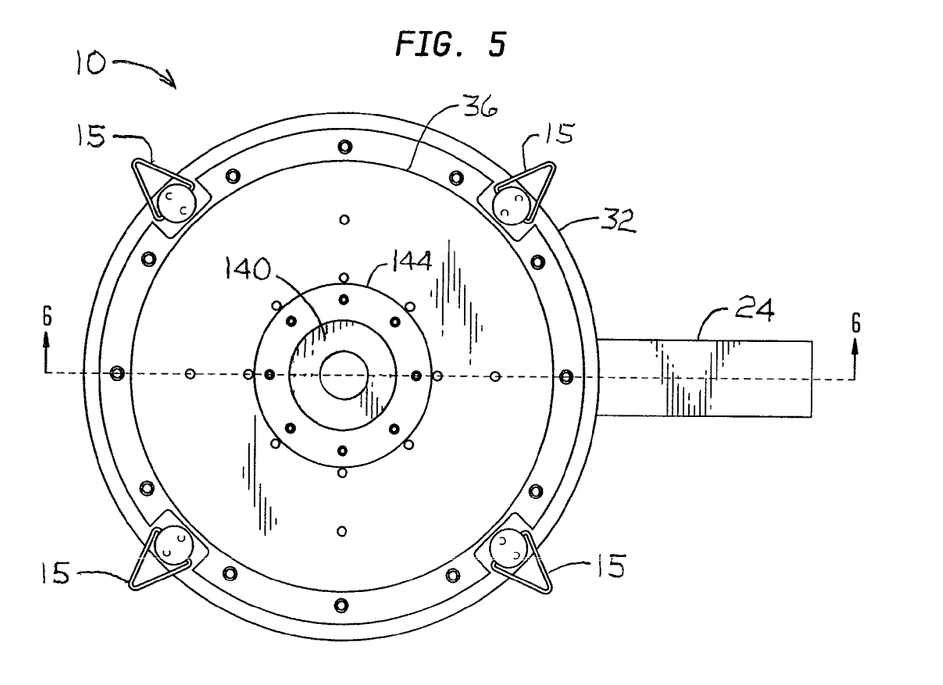
FIG. 5 is a top plan view of the example magnetic flux leakage inspection apparatus in FIG. 1.

Referring again to FIG. 6 in combination with FIGS. 1-5 and 7, all of the electric components and exposed wiring for powering the coil 60 and sensors 70, 80 and electronic components 81 in the MFL inspection apparatus 10 for reading, processing, or transmitting data from the detector assemblies 72, 82 are positioned in the hermetically sealed interior chamber 40, so that they will not be exposed to any flammable gases, liquids, or other substances that may get into the central channel 12 or that may be present in the proximate environment outside the MFL inspection apparatus 10. The high power wires or cords 110, 112 that carry electric power to power the coil 60 and other electrical components are connected to wires 114, 116 in the interior chamber 40 with explosion-proof connectors 118, 120. The shield 24 protects the connectors 118, 120 from accidental impacts by other equipment, tubing joints, and the like, as mentioned above. The shield 24 can be permanently or removably attached to the barrel wall 30 or other structure, for example with a J-hook slot 126 and pin 128 arrangement, as shown in FIG. 3.

As also mentioned above, the interior chamber 40 can be pressurized with air or other inert gas under pressure through an inlet port 130 and connector 132, which can be a standard connector for connecting the port 130 to a supply hose 26. A pressure relief or regulator valve 134 can be provided on another port (see, e.g., FIG. 2) or, for another example, on a tee fitting (not shown) connected to the connector 132 for regulating the pressure in the interior chamber 40 at a desired pressure. For example, positive pressure of about 25 to 50 psi is sufficient to supplement the seals in ensuring that no flammable gases, liquids, or other substances flow or migrate from the central channel 12 or from outside the MFL inspection apparatus 10 into the interior chamber 40 during operation of the MFL inspection apparatus 10. A purge port 136 and valve 138 can also be provided to purge the air or inert gas along with any other gases or vapors out of the interior chamber 40, for example, at the beginning or at the end of an operation as an additional precaution against any build-up or accumulation of a flammable gas, liquid, or other substance in the interior chamber 40.

While a number of example aspects and implementations have been discussed above, those of skill in the art will recognize certain modifications, permutations, additions and sub-combinations thereof. It is therefore intended that the following appended claims and claims hereafter introduced are interpreted to include all of these and other modifications, permutations, additions and sub-combinations as are within the spirit and scope of the claims. The words "comprise", "comprises", "comprising", "composed", "composes", "composing", "include", "including", "includes", "contain", "contains", "containing", "carry", "carries", "carrying", "involve", "involves", "involving", "have", "has", and "having" when used in this specification, including the claims, are open-ended in the sense of meaning including but not limited to, i.e., intended to specify the presence of stated features, integers, components, or steps, but they do not preclude the presence or addition of one or more other features, integers, components, steps, or groups thereof Only the transitional phrases "consisting of" and "consisting essentially of", if used in this specification, including the claims, would be considered as closed or semi-closed transitional phrases. Also, use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Also, in the specification, as a number of an item, feature, element, or component is open-ended and means that number or more, e.g., "at least one", "at least two", "at least three", etc., unless explicably stated otherwise, e.g., as "only [number]" or "no more than [number]".

The invention and several embodiments in which an exclusive property or privilege is claimed are defined as follows:

1. Magnetic flux leakage inspection apparatus for inspecting well tubing for flaws, comprising:
    a hermetically sealed interior chamber that is closed and hermetically sealed by an outer wall, a top closure, a bottom closure, and an inner wall assembly, wherein the inner wall assembly includes a conduit of non-magnetic material that forms and surrounds a central channel in a manner that separates the central channel from the hermetically sealed interior chamber around the inner wall assembly, said central channel having an open top and an open bottom to accommodate passage of the well tubing through the central channel, and wherein the magnetic flux leakage inspection apparatus also has an inlet port for applying pressurized air or inert gas into the hermetically sealed interior chamber;
    an electromagnetic coil and electrical components and wiring for powering the electromagnetic coil are all positioned inside the hermetically sealed interior chamber with the electromagnetic coil surrounding the conduit of the inner wall assembly for creating a magnetic field in the central channel to magnetize well tubing in the central channel;
    a magnetic flux leakage detector assembly and electrical components for powering the magnetic flux leakage detector assembly are all positioned inside the hermetically sealed interior chamber with the magnetic flux leakage detector assembly positioned around the conduit of the inner wall assembly for detecting magnetic flux leakage from magnetized well tubing in the central channel; and
    a shallow reading detector assembly and electrical components for powering the shallow reading detector assembly are all positioned inside the hermetically sealed interior chamber with the shallow reading detector assembly positioned around the conduit of the inner wall assembly.

2. The magnetic flux leakage inspection apparatus of claim 1, including seals between the outer wall and the top closure, between the outer wall and the bottom closure, between the inner wall assembly and the top closure, and between the inner wall assembly and the bottom closure, to seal the inner chamber from the central channel and environment outside of the inner chamber.

3. The magnetic flux leakage inspection apparatus of claim 1, wherein the magnetic flux leakage detector assembly includes a split-ring magnetic flux detector assembly comprising two interfacing half-ring sections mounted on the conduit of the inner wall assembly around the central channel, each of the half-ring sections having an arcuate cavity and a plurality of Hall effect sensors mounted in a semi-circular arc on a printed circuit board positioned in the cavity.

4. Magnetic flux leakage inspection apparatus for inspecting well tubing for flaws, comprising:

a hermetically sealed interior chamber that is closed and hermetically sealed by an outer wall, a top closure, a bottom closure, and an inner wall assembly, wherein the inner wall assembly includes a conduit that forms and surrounds a central channel in a manner that separates the central channel from the hermetically sealed interior chamber around the inner wall assembly, said conduit having an open top and an open bottom to accommodate passage of the well tubing through the central channel;

a magnetic flux leakage detector assembly positioned inside the hermetically sealed interior chamber around the conduit of the inner wall assembly for detecting magnetic flux leakage from magnetized well tubing in the central channel, wherein the magnetic flux leakage detector assembly includes a split-ring magnetic flux detector assembly comprising two interfacing half-ring sections mounted on the conduit of the inner wall assembly around the central channel, each of the half-ring sections having an arcuate cavity and a plurality of Hall effect sensors mounted in a semi-circular arc on a printed circuit board positioned in the cavity, and wherein said conduit has a circumferential groove that is sized and shaped to receive the half-ring sections of the split-ring magnetic flux detector assembly, and the split-ring magnetic detector assembly is mounted in the groove to encircle the central channel; and a shallow reading detector assembly positioned inside the hermetically sealed interior chamber around the conduit of the inner wall assembly.

5. The magnetic flux leakage inspection apparatus of claim 4, wherein the conduit has a second circumferential groove, the shallow reading detector assembly includes a split-ring shallow reading detector assembly comprising two interfacing half-ring sections mounted in the second circumferential groove around the central channel, each of the half-ring sections of the shallow reading detector assembly having an arcuate cavity and a plurality of shallow reading sensors mounted in a semi-circular arc on a printed circuit board positioned in the cavity.

* * * * *